(12) United States Patent
Qiao et al.

(10) Patent No.: US 8,809,036 B2
(45) Date of Patent: Aug. 19, 2014

(54) **SECRETION EXPRESSION OF ANTIBIOTIC PEPTIDE CAD IN *BACILLUS SUBTILIS* AND EXPRESSION SYSTEM OF RECOMBINATION *BACILLUS SUBTILIS***

(75) Inventors: Shiyan Qiao, Beijing (CN); Faming Zhu, Beijing (CN); Wenjiang Guo, Beijing (CN)

(73) Assignee: Peking Sinagri Yin Thai Biotechnology Co. Ltd., Zhongguancun Biomedical Garden, Haidan District, Beijing (CN)

( * ) Notice: Subject to any disclaimer, the term of this patent is extended or adjusted under 35 U.S.C. 154(b) by 12 days.

(21) Appl. No.: 13/054,928

(22) PCT Filed: Jul. 21, 2009

(86) PCT No.: PCT/CN2009/000815
§ 371 (c)(1),
(2), (4) Date: Apr. 12, 2011

(87) PCT Pub. No.: WO2010/009614
PCT Pub. Date: Jan. 28, 2010

(65) Prior Publication Data
US 2012/0009625 A1    Jan. 12, 2012

(30) Foreign Application Priority Data
Jul. 22, 2008 (CN) .......................... 2008 1 0132258

(51) Int. Cl.
*C12N 15/09* (2006.01)
*C12N 9/54* (2006.01)
*A61K 38/00* (2006.01)

(52) U.S. Cl.
USPC .................. 435/252.31; 424/192.1; 536/23.4; 530/350; 530/387.3; 435/221; 435/252.3; 435/172.1

(58) Field of Classification Search
None
See application file for complete search history.

(56) References Cited

U.S. PATENT DOCUMENTS

2004/0235176 A1* 11/2004 Jo et al. .......................... 435/471
2006/0134630 A1    6/2006 Segura et al.
2008/0241887 A1* 10/2008 Viksoe-Nielsen et al. ...... 435/72

FOREIGN PATENT DOCUMENTS

CN   101182351 A   5/2008
CN   101307316 A   11/2008

OTHER PUBLICATIONS

Huang Ya-Dong et al, "Modification of cecropin AD gene and its expression in *Pichia pastoris*", Journal of South China University of Technology (Natural Science Edition) . . . vol. 30, No. 2, Feb. 28, 2002, ISSN: 1000-565X, See whole document, (2002).

* cited by examiner

*Primary Examiner* — Manjunath Rao
*Assistant Examiner* — Samuel Liu
(74) *Attorney, Agent, or Firm* — Yi Chen; Novak Druce Connolly Bove + Quigg LLP

(57) ABSTRACT

The present invention relates to a method for expressing antimicrobial peptide CAD by means of a recombinant *Bacillus subtilis* expression system. The SUMO protease expression operon is first artificially synthesized. The protein expression operon genes of *Saccharomyces cerevisiae* small ubiquitin-related protein is then fused with the antibacterial peptide AD. The fusion protein is further cloned into the pNF11 plamid to be introduced into *Bacillus subtilis*, thereby ensuring the induced expression of recombined *Bacillus subtilis* in shake flasks. The method has the advantages of a simple expression system, large-scale production, low production cost, strong biological activity and no toxic or harmful substance production. Moreover, the method provides a medicine with low price and strong antibacterial capacity for clinic disease prevention and treatment. This invention can also be used as a feedstuff additive.

2 Claims, 2 Drawing Sheets

SEQUENCE LISTING

<160> NUMBER OF SEQ ID NOS: 8

<210> SEQ ID NO 1
<211> LENGTH: 747
<212> TYPE: DNA
<213> ORGANISM: ARTIFICIAL SEQUENCE
<220> FEATURE:
<223> OTHER INFORMATION: RECOMBINANT BACILLUS SUBTILIS

<400> SEQUENCE: 1

```
atggtcagca tccgccgcag cttcgaagcg tatgtcgatg acatgaatat cattactgtt      60
ctgattcctg ctgaacaaaa ggaaatcatg cttgttccgg aacttaatga aaagatgat     120 gatcaagttc aaaaagcact tgcatctaga gaaaatacac aacttatgaa tagagataat    180
attgaaatta cagttagaga ttttaaaaca cttgcaccga gaagatggct taatgataca    240
attattgaat tttttatgaa atatattgaa aaatctacac cgaatacagt tgcatttaat    300 tcttttttt atacaaatct ttctgaaaga ggctatcaag gcgttagaag atggatgaaa    360
agaaaaaaaa cacaaattga taaacttgat aaaattttta caccgattaa tcttaatcaa    420
tctcattggg cacttggcat tatttgatctt aaaaaaaaaa caattggcta tgttgattct    480
ctttctaatg gcccgaatgc aatgtctttt gcaattctta cagatcttca aaaatatgtt    540
atggaagaat ctaaacatac aattggcgaa gattttgatc ttattcatct tgattgcccg    600
caacaaccga atggctatga ttgcggcatt tatgtttgca tgaatacact ttatggctct    660
gcagatgcac cgcttgattt tgattataaa gatgcaatta gaatgagaag atttattgca    720
catcttattc ttacagatgc acttaaa                                         747
```

<210> SEQ ID NO 2
<211> LENGTH: 738
<212> TYPE: DNA
<213> ORGANISM: ARTIFICIAL SEQUENCE
<220> FEATURE:
<223> OTHER INFORMATION: RECOMBINANT BACILLUS SUBTILIS

<400> SEQUENCE: 2

```
taaaaaaaac gctcacatga tgtgggcgtt tttttatac aaaaaaacgc actgatttac      60
aaaaccttaa cattcggttc aaaccctttt tacatagaac ctttactcta tacgtgtagg    120
acaaattaca cattatacgc aggggatggt cagcatccgc cgcagcttcg aagcgtatgt    180
cgatgacatg aatatcatta ctgttctgat tcctgctgaa caaaggaaa tcatgatgtc     240 tgcaaatcaa gaagaagata aaaaaccggg cgatggcggc gcacatatta atcttaaagt   300
taaaggccaa gatggcaatg aagtttttt tagaattaaa agaagcacac aacttaaaaa    360
acttatgaat gcatattgcg atagacaatc tgttgatatg aatagcattg catttctttt   420
tgatggcaga agacttagag cagaacaaac accggatgaa cttgatatgg aagatggcga   480
tgaaattgat gcaatgcttc atcaaacagg cggcagcggc ggcggcgcaa cagcaaaatg   540
gaaacttttt aaaaaaattg aaaaagttgg ccaaagagtt agagatgcag ttatttctgc   600
aggcccggca gttgcaacag ttgcacaagc aacagcactt gcaaaataaa aggagctgac   660
cgaacagggc agctccttta atagcacttt gccactcatt ttttgcgtta gcaaaaacat   720
aaagggtatg ggatataa                                                  738

<210> SEQ ID NO 3
<211> LENGTH: 59
<212> TYPE: DNA
<213> ORGANISM: ARTIFICIAL SEQUENCE
<220> FEATURE:
<223> OTHER INFORMATION: RECOMBINANT BACILLUS SUBTILIS

<400> SEQUENCE: 3
ctttttttta tacaaatctt tctgaaagag gctatcaagg cgttagaaga tggatgaaa     59

<210> SEQ ID NO 4
<211> LENGTH: 59
<212> TYPE: DNA
<213> ORGANISM: ARTIFICIAL SEQUENCE
<220> FEATURE:
<223> OTHER INFORMATION: RECOMBINANT BACILLUS SUBTILIS

<400> SEQUENCE: 4
tcaagtttat caatttgtgt tttttttctt ttcatccatc ttctaacgcc ttgatagcc     59

<210> SEQ ID NO 5
<211> LENGTH: 58
<212> TYPE: DNA
<213> ORGANISM: ARTIFICIAL SEQUENCE
<220> FEATURE:
<223> OTHER INFORMATION: RECOMBINANT BACILLUS SUBTILIS

<400> SEQUENCE: 5
cgatggcggc gcacatatta atcttaaagt taaaggccaa gatggcaatg aagttttt      58

<210> SEQ ID NO 6
<211> LENGTH: 59
<212> TYPE: DNA
<213> ORGANISM: ARTIFICIAL SEQUENCE
<220> FEATURE:
<223> OTHER INFORMATION: RECOMBINANT BACILLUS SUBTILIS

<400> SEQUENCE: 6
ttttaagttg tgtgcttctt ttaattctaa aaaaaacttc attgccatct tggcccttta    59

<210> SEQ ID NO 7
<211> LENGTH: 21
<212> TYPE: DNA
<213> ORGANISM: ARTIFICIAL SEQUENCE
```

```
-continued

<220> FEATURE:
<223> OTHER INFORMATION: RECOMBINANT BACILLUS SUBTILIS

<400> SEQUENCE: 7
cgtttgcgct tgttccggaa c                                              21

<210> SEQ ID NO 8
<211> LENGTH: 21
<212> TYPE: DNA
<213> ORGANISM: ARTIFICIAL SEQUENCE
<220> FEATURE:
<223> OTHER INFORMATION: RECOMBINANT BACILLUS SUBTILIS

<400> SEQUENCE: 8
cgtttgcgct tgttccggaa c                                              21
```

SECRETION EXPRESSION OF ANTIBIOTIC PEPTIDE CAD IN *BACILLUS SUBTILIS* AND EXPRESSION SYSTEM OF RECOMBINATION *BACILLUS SUBTILIS*

FIELD OF THE INVENTION

The present invention relates to a method of producing antimicrobial peptide CAD, and specifically relates to a method of expressing the antimicrobial peptide CAD based on a recombinant *Bacillus subtilis* expression system.

BACKGROUND OF THE INVENTION

Insect antimicrobial peptide is a class of small-molecule alkaline polypeptide, which has heat stability, "non-specific inducibility and a broad-bactericidal spectrum". It is promising to develop a new type of polypeptide antibiotic with insect antimicrobial peptide. It is known that about 15-20 kinds of bactericidal proteins, which include lysozyme, attacin, antibacterial peptide and other three classes, are produced in the haemolymph of virus infected *Hyolophora cecropia* (Hultmark D. et al, *Eur. J. Biochem.* 106: 7-16, 1980). According to small differences of the primary structure, *Hyolophora cecropia* is classified under three types: A, B and D (Hultmark D, same as above). Besides, a series of similar antimicrobial peptides have been separated from Chinese *Antheraea pernyi*. These polypeptides, which are obtained from various insects and can kill plant pathogens, are collectively referred to as antimicrobial peptides. Their amino acid sequences have high homology with each other, and there are large numbers of hydrophilic amino acid residues, especially lysine, arginine and alkaline amino acids in these molecules, while there are much more hydrophobic residues at C-end. Moreover, there are lots of conserved amino acid residues at many specific positions within the polypeptides, such as tryptophan in position 2, lysine in position 5, 8 and 9, aspartate in position 11 and 20 and so on (Steiner H. et al, *Nature* 292: 246-248, 1981).

In the world, many researches on antimicrobial peptide genes engineering have been carried out because antimicrobial peptides have a large potential as sterilizing or anti-tumor agent and in inhibiting virus copies. Up to now, expression researches on antimicrobial peptide genes in the *Colibacillus*, yeasts and baculovirus carriers have been reported.

"Study on expression of antibacterial peptide AD genes in AcNPV vector expression system" (Huang Ya-dong, *Chinese Journal of Antibiotics*, 28:304-307, 2003) reported a method of studying antibacterial peptide AD (CAD) genes expression "in insect culture cell" and insect by baculovirus vector system. CAD genes were modified by polymerase chain reaction (PCR) amplification. The modified CAD genes were first cloned into plasmid pGEM-T easy vector for identification and sequence analysis, and then subcloned into *Autographa californica* nuclear polyhedrosis virus (AcNPV) vector pAcGP67B to obtain a recombinant virus vector. *Spodoptera frugiperododa* Sf9 cells were co-infected with a recombinant virus vector and wild type AcNPVDNA, and recombinant viruses were screened through Sea Plaque screening. Sf9 cell and *Autographa californica* young larvae were transfected by the recombinant virus AcNPVAD, the CAD genes which were used for antibacterial activity test have been confirmed to be expressed in baculovirus carriers system, and the expression products has antibacterial activity.

The publication "Modification of antibacterial peptide AD genes and its expression in *Pichia pastoris*" (Huang Ya-dong, *Journal of South China University of Technology* (Natural Science Edition) 30: 13-16, 2003) reported that antibacterial peptide AD genes were amplified and modified with Asn codon added to its C terminal end by PCR. The modified antibacterial peptide AD genes were cloned into the integrative plasmid pPICZ-A to construct a recombinant expression vector, and then transformed into *Pichia pastoris* host bacterium GS115. The recombinant transformants were screened by using a selective agar media that contains a zeocin resistant mark. After fermentation, the concentrate was analyzed and tested on acidic-PAGE for its antibacterial activity. The results showed that antibacterial peptide AD genes was successfully expressed in *Pichia pastoris*. The expression product was secreted outside with the guidance of a factor signal and had a strong antibacterial activity.

The patent ZL96100376.6 disclosed four kinds of polypeptides or derivatives with antibacterial activity and antimicrobial peptide production methods thereof in cultured cells such as *Colibacillus* cells, yeast cells, plant cells, insect cells, mammalian cells and so on.

All of the above mentioned methods use cultured virus, *Colibacillus* cells, yeast cells, plant cells, insect cells, mammalian cells and so on for expressing genes coding antimicrobial peptides. But there are some disadvantages using virus vector system to express the objective proteins like:

cumbersome experimental procedures, difficulties to control the experimental conditions, not suitable for mass production.

Antimicrobial peptide had inhibiting effect on bacteria such as *E. coli*. So *E. coli*, as a prokaryote, was difficult to use as an expression system. Although antimicrobial peptide had no inhibiting effect on eukaryotic cells, studies showed that it was difficult to achieve high-density cultivation, and had a greater impact on improving the expression level in yeast. Moreover, its amidation in yeast was incomplete, which had some impacts on its sterilizing activity. Moreover, the eukaryotic cells expression system had the disadvantage of long production cycles and high production costs.

SUMMARY OF THE INVENTION

The objective of the present invention is to provide a production method for genetic engineering of antimicrobial peptide CAD with a broad spectrum antibacterial activity to overcome the disadvantages of current antimicrobial peptide industrialization, and provide a cheaper and a most efficient antimicrobial medicine for disease prevention and treatment. It can also be used as a harmless feed additive. Until now, the expression of antimicrobial peptide CAD in *Bacillus subtilis* has not been reported yet. The *Bacillus subtilis* is characterized by easy culture conditions, high propagation speed, and high secretion. Furthermore, it is a prokaryotic cell type.

With this aim in view, the present invention comprises:

1. The synthesis of the small ubiquitin-related modifier (SUMO) protease expression operon genes, the fusion of protein expression operon genes of *Saccharomyces cerevisiae* small ubiquitin-related protein with antibacterial peptide AD:

a) the nucleotide sequence of artificial synthesis expression operon genes with coding SUMO protease is listed below (SEQ ID NO. 1):

```
       10         20         30         40         50
atggtcagca tccgccgcag cttcgaagcg tatgtcgatg acatgaatat 60         70         80         90        100
cattactgtt ctgattcctg ctgaacaaaa ggaaatcatg cttgttccgg 110        120        130        140        150
aacttaatga aaaagatgat gatcaagttc aaaaagcact tgcatctaga 160        170        180        190        200
gaaaatacac aacttatgaa tagagataat attgaaatta cagttagaga 210        220        230        240        250
ttttaaaaca cttgcaccga gaagatggct taatgataca attattgaat 260        270        280        290        300
tttttatgaa atatattgaa aaatctacac cgaatacagt tgcatttaat 310        320        330        340        350
tcttttttt atacaaatct ttctgaaaga ggctatcaag gcgttagaag 360        370        380        390        400
atggatgaaa agaaaaaaaa cacaaattga taaacttgat aaaatttta 410        420        430        440        450
caccgattaa tcttaatcaa tctcattggg cacttggcat tattgatctt 460        470        480        490        500
aaaaaaaaaa caattggcta tgttgattct ctttctaatg gcccgaatgc 510        520        530        540        550
aatgtctttt gcaattctta cagatcttca aaaatatgtt atggaagaat 560        570        580        590        600
ctaaacatac aattggcgaa gattttgatc ttattcatct tgattgcccg 610        620        630        640        650
caacaaccga atggctatga ttgcggcatt tatgtttgca tgaatacact 660        670        680        690        700
ttatggctct gcagatgcac cgcttgattt tgattataaa gatgcaatta 710        720        730        740        747
gaatgagaag atttattgca catcttattc ttacagatgc acttaaa
``` b) the nucleotide sequence of artificial synthesis fusion protein expression operon genes with coding *Saccharomyces cerevisiae* ubiquitin-like small molecule protein and antibacterial peptide AD is listed below (SEQ ID NO. 2):

```
       10         20         30         40         50
taaaaaaaac gctcacatga tgtgggcgtt ttttttatac aaaaaaacgc 60         70         80         90        100
actgatttac aaaaccttaa cattcggttc aaacccttt tacatagaac 110        120        130        140        150
ctttactcta tacgtgtagg acaaattaca cattatacgc aggggatggt 160        170        180        190        200
cagcatccgc cgcagcttcg aagcgtatgt cgatgacatg aatatcatta 210        220        230        240        250
ctgttctgat tcctgctgaa caaaaggaaa tcatgatgtc tgcaaatcaa 260        270        280        290        300
gaagaagata aaaaaccggg cgatggcggc gcacatatta atcttaaagt 310        320        330        340        350
taaaggccaa gatggcaatg aagtttttt tagaattaaa agaagcacac 360        370        380        390        400
aacttaaaaa acttatgaat gcatattgcg atagacaatc tgttgatatg 410        420        430        440        450
aatagcattg catttctttt tgatggcaga agacttagag cagaacaaac
```

```
                         -continued
460        470        480        490        500
accggatgaa cttgatatgg aagatggcga tgaaattgat gcaatgcttc 510        520        530        540        550
atcaaacagg cggcagcggc ggcggcgcaa cagcaaaatg gaaacttttt 560        570        580        590        600
aaaaaaattg aaaagttgg  ccaaagagtt agagatgcag ttatttctgc 610        620        630        640        650
aggcccggca gttgcaacag ttgcacaagc aacagcactt gcaaaataaa 660        670        680        690        700
aggagctgac cgaacagggc agctccttta atagcactt  gccactcatt 710        720        730        738
ttttgcgtta gcaaaaacat aaagggtatg ggatataa
``` c) the construction of said artificial genes fragments in steps a) with a first enzymatic double-cleavage performed by EcoR/and BamHI and in steps b) with a second enzymatic double cleavage performed by BamHI and SacI respectively into vector pBluescriptII SK(+). This construction is named plasmid D1778-1.

2. The construction of the *Bacillus Subtilis* expression vector pNF11 of the antibacterial peptide AD matrix genes comprises the following steps;

the genome extraction of *Bacillus subtilis* strain 168, the amplification of its high-active promoter p43, after PCR, the amplified promoter is recovered and sequenced. It is then subcloned into the T vector. The T vector is then used to introduce the promoter into the pGJ103 plasmid, thus forming the pGJ284 plasmid;

the double enzymatic restriction of the plasmids pGJ284 and plasmid D1778-1 is carried out by respectively EcorI and Sac I.

Then, the products are recovered, and linked with the ligase T4DNA in water-bath at 16° C. to get the recombinant plasmid pNF11.

3. The transformation of recombinant expression vector pNF11 in the *Bacillus subtilis* 1A747 can be achieved with the following procedure;

mix competent *Bacillus subtilis* 1A747 with plasmid pNF11, and transfer the mixture into a 0.2 cm electroporation cup, 2500V, shock for 5 minutes, add 800 μl of cold electroporation recovery medium LBSPG on *Bacillus subtilis* immediately, recover and cultivate for 1 hour at 37° C., 200 rpm, centrifuge the colonies at 4500 rpm and coat on a Cm5LB plate for further cultivation at 37° C. until single colonies appear, pick up the positive transformants for cultivation extract plasmids to carry out a double-enzyme cleavage with EcoRI and SacI and PCR identification;

The amplified 1300 base pairs (bp) clones are defined as pNF11-CAD1, pNF11-CAD2, pNF11-CAD3, pNF11-CAD4 positive transformants.

4. Inducible expression of the recombinant *Bacillus subtilis* in shake flasks:

The pNF11-CAD1, pNF11-CAD2, pNF11-CAD3 and pNF11-CAD4 positive transformants are inoculated in 25 ml LB culture medium, and cultivated for 8-12 h at 32° C., 200 rpm until the absorbance of the 600 nm waves up to 2~4. Then, 5 ml 30 wt % maltose are added to the culture for inducible expression at 32° C., 250 rpm, for 24-36 h with shaking. pH is set at 8.5 before cultivation for 8-12 h at 25° C. The culture medium is then centrifuged for 10 minutes at 10000 rpm. Finally, the supernatant containing the antimicrobial peptide CAD protein is gathered.

A *Bacillus subtilis* recombining the expression vector expressing an antimicrobial peptide CAD of the present invention is preserved at the China General Microbiological Culture Collection Center, and the culture collection code is CGMCC No. 2373. It is the positive converter that recombinant plasmid pNF11 transformed from the *Bacillus subtilis* 1A747.

The present invention relates as well to a *Bacillus subtilis* strain recombining the expression vector of the antimicrobial peptide CAD, the code of which is CGMCC No. 2373.

According to the expression demand, the value of pH during fermentation and culture is set for six grades (6.5, 7.0, 7.5, 8.0, 8.5, 9.0). From the growth curve, we found that the optimal growth period is 36 h under the six-grades pH. The protein expression level is the highest under these conditions.

The artificial bicistronic expression elements genes of the present invention contain the small ubiquitin-related modifier (SUMO) protease fused with the bicistronic expression elements of the antimicrobial peptide CAD. This fusion gene is used to construct an antimicrobial peptide CAD recombinant *Bacillus subtilis* expression system based on plasmid pNF11-CAD for *Colibacillus-Bacillus subtilis* shuttle vector. This system has a great plasmid stability, and SUMO-CAD protein conjugates can be hydrolyzed into antimicrobial peptide CAD by the SUMO protease expression.

In order to secrete active antimicrobial peptide CAD, the present invention adopts an expression system that fuses *Bacillus subtilis* with the SUMO. The CAD-SUMO fusion products have no antibacterial activity. There is no harmful effect on the host bacterium. Therefore, the host can express the fusion protein for a long time continuously. The substrate fusion protein needs to be hydrolyzed by the SUMO protease in order to produce the active antimicrobial peptide CAD substrate. As the SUMO protease is very expensive, the present invention adopts the bicistronic expression system in which the host bacterium is induced to produce protease by the SUMO. Bacteria recombining the CAD-SUMO fusion genes are cultivated to express the CAD-SUMO fusion proteins before induction. The induction consists in setting the culture conditions to allow the SUMO protease activation and therefore the hydrolysis of the chimera to release the antimicrobial peptide CAD. The use of *Bacillus subtilis* as host permits to reach high levels of expression of the fusion protein.

This system overcomes a lot of antibacterial peptides industrial problems like:
high cost of chemical synthesis of the peptides,
difficulties to industrial application because of the antibacterial and anti-virus capability of antibacterial peptides, making it difficult to use the common bacteria or viruses as an expression system,
expensive fusion expression inducers,
complex separation and purification technology, and low gene expression yield.

There are some advantages of the present invention in the following:
1. a simple expression system: this present invention adopts the fusion expression system of *Bacillus subtilis* recombining the antimicrobial peptide CAD with the SUMO. Because the fusion products have no antibacterial activity, there is no harmful effect on the host bacterium 1A747. It ensures the bacteria to express the fusion proteins continuously without inhibition for the host bacterium;
2. the present invention is suitable for a large-scale production. This invention adopts the *Bacillus subtilis* expression system. Its production conditions and steps are much easier than eukaryotic expression system, and its reaction conditions are easy to control;
3. low production cost: the medium used for the present invention is much cheaper, the production devices are all conventional laboratory devices, and the procedure is easy to operate;
4. the product get by the present invention process has a high protein concentration and strong biological activity; and
5. easier hydrolysis by the protease due to its smaller molecular weight.

BRIEF DESCRIPTION OF THE DRAWINGS

FIG. 1(1) shows the inhibition zone of recombinant *Bacillus subtilis* against *Colibacillus* K88 as FIG. 1 shown;
FIG. 1(2) shows the inhibition zone of recombinant *Bacillus subtilis* against *Staphylococcus aureus* as FIG. 1 shown;
FIG. 1(3) shows the inhibition zone of recombinant *Bacillus subtilis* against *Salmonella typhi* as FIGS. 1 and 2 shown;
FIG. 1(4) shows the inhibition zone of recombinant *Bacillus subtilis* against *Enterococcus faecalis* as FIGS. 1, 2 and 3 shown;
FIG. 1(5) shows the inhibition zone of recombinant *Bacillus subtilis* against *Streptococcus faecalis* as FIGS. 1, 2 and 3 shown.

DETAILED DESCRIPTION OF EMBODIMENTS

Example 1

Figure 1:
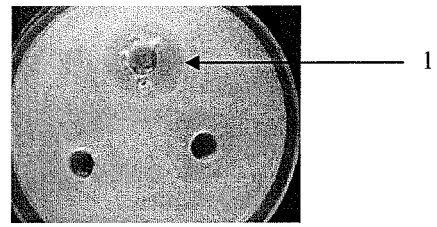
FIG. 1 shows the inhibition zone of antimicrobial peptide CAD.
Figure 1:
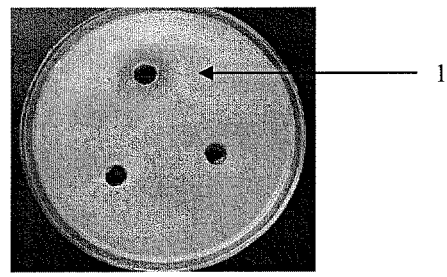
Figure 1:
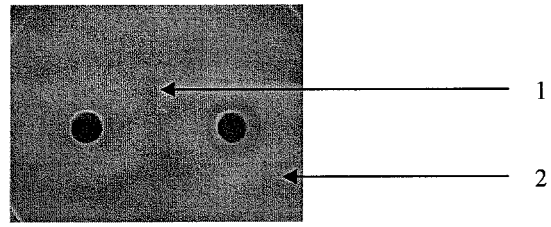
Figure 1:
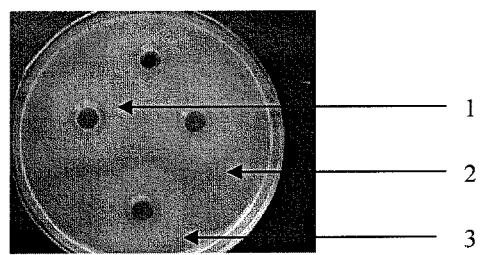
Figure 1:
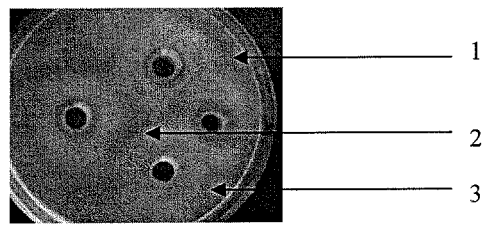

1. Synthesis of the SUMO protease expression operon genes and fusion of the protein expression operon genes of *Saccharomyces cerevisiae* small ubiquitin-related protein with the antibacterial peptide AD;

1) the artificial synthesis of coding SUMO protease expression operon genes, and its inducer is as follows:
Designed inducer is as follows:

F1 (SEQ ID NO. 3):
CTTTTTTTTATACAAATCTTTCTGAAAGAGGCTATCAAGGCGTTAGAAG
ATGGATGAAA

R1 (SEQ ID NO. 4):
TCAAGTTTATCAATTTGTGTTTTTTTTCTTTTCATCCATCTTCTAACGC
CTTGATAGCC and it is synthesized through 5 times PCR reaction recycles.
The PCR reaction system contains: inducer 2 µl (10 µmol/L), 5 µl dNTP Mixture (2.5 mmol/L), 5 µl 10× Buffer, 35.7 µl sterile ddH$_2$O;
The PCR reaction conditions are: a first denaturation step at 94° C. for 5 minutes; slowly cooling down to 55° C.; addition of 0.3 µl Pyrobest DNA and polymerase (5 U/µl) respectively; and then extension at 72° C. for 5 minutes;
2) The artificial synthesis of coding *Saccharomyces cerevisiae* ubiquitin-like small molecule protein and antibacterial peptide AD fusion protein expression operon genes, and its inducer is as follows:
Designed inducer—

F1 (SEQ ID NO. 5):
CGATGGCGGCGCACATATTAATCTTAAAGTTAAAGGCCAAGATGGCAAT
GAAGTTTTT

R1 (SEQ ID NO. 6):
TTTTAAGTTGTGTGCTTCTTTTAATTCTAAAAAAAACTTCATTGCCATC
TTGGCCTTTA

And it is synthesized through 5 times PCR reaction cycles.
The PCR reaction mix contains: inducer 2 µl (10 µmol/L), 5 µl dNTP Mix (2.5 mmol/L), 5 µl 10× Buffer, 35.7 µl sterile ddH$_2$O;
The PCR reaction conditions are as follows: denaturation at 94° C. for 5 minutes; slowly cooling down to 55° C.; addition of 0.3 µl Pyrobest DNA and polymerase (5 U/µl) respectively; and then extension at 72° C. for 5 min;
3) The construction of the two artificial fragments into vector pBluescriptII SK(+) as follows:
The first step is the construction of said artificial genes fragments in step a) with a first enzymatic double-cleavage performed by EcoRI and BamHI and in step b) with a second enzymatic double cleavage performed by BamHI and Sac I respectively. These fragments are then introduced into vector pBluescriptII SK(+). This construction is named plasmid D1778-1.2.
The construction of the *Bacillus subtilis* expression vector pNF11 of the antibacterial peptide AD matrix genes comprises the following steps:
the genome extraction of *Bacillus subtilis* strain 168, and the amplification of its high active promoter p43;
after PCR, the amplified promoter is recovered and sequenced. It is then subcloned into the T vector. The T vector is then used to introduce the promoter into the pGJ103 plasmid, thus forming the pGJ284 plasmid;
the double enzymatic restriction of the plasmids pGJ284 and plasmid D1778-1 is carried out by respectively EcorI and Sac I,
Then, the products are recovered and linked with the ligase T4DNA in water-bath at 16° C. to get the recombinant plasmid pNF11.

Said PCR identification inducers are listed below:

```
F1 (SEQ ID NO. 7): CGTTTGCGCTTGTTCCGGAAC
R1 (SEQ ID NO. 8): CTGCCGGGCCTGCAGAAATAAC
```

The PCR amplification system includes:
plasmid pNF11 template 2 μl;
dNTP, 2.5 mmol/L, 3 μl;
LA taq polymerase buffer, 2.5 μl;
F1, 1.5 μl;
R1, 1.5 μl;
LA taq polymerase, 0.3 μl;
Sterile ultra-pure water, 14.2 μl;
The PCR reaction conditions are: pre-denaturation at 94° C. for 3 minutes, and into the PCR cycle: denaturation at 94° C. for 30 seconds, then cool down at 56° C. 30 seconds, elongation at 72° C. for 3 minutes, for 35 cycles total; and then final elongation at 72° C. for 10 minutes. Thus 1300 bases pairs (bp) clone segments are amplified.

3. The transformation of recombinant expression vector pNF11 in the *Bacillus subtilis* 1A747 can be achieved through the following procedure:
   mix 80 μl of the competent *Bacillus subtilis* 1A747 with 5 μl of plasmid pNF11,
   transfer the mixture into a 0.2 cm electroporation cup, 2500V, shock for 5 minutes,
   add 800 μl of cold electroporation recovery medium LBSPG immediately, recover and cultivate for 1 hour at 37° C., 200 rpm,
   centrifuge the colonies at 4500 rpm and coat on a Cm5LB plate for further cultivation at 37° C. until single colonies appeared,
   pick up the positive transformants to cultivate and extract the plasmids to carry out the double digestion with Ecor I and Sac I and for PCR identification. The amplified 1300 base pairs (bp) clones are defined as pNF11-CAD1, pNF11-CAD2, pNF11-CAD3, pNF11-CAD4 positive transformants.

4. Inducible expression of the recombinant *Bacillus subtilis* in shake flasks:
   The pNF11-CAD1, pNF11-CAD2, pNF11-CAD3 and pNF11-CAD4 positive transformants are inoculated in 25 ml LB culture medium, and cultivated for 12 hours at 32° C., 200 rpm until the absorbance of the 600 nm waves up to 2~4. Then, 5 ml 30 wt % maltose are added to the culture for inducible expression at 32° C., 250 rpm, for 36 hours with shaking. pH is set at 8.5 before cultivation for 12 hours at 25° C. The culture medium is then centrifuged for 10 minutes at 10000 rpm. Finally, the supernatant containing the antimicrobial peptide CAD protein is gathered.

Example 2

Identification of Antibacterial Activity of the Antimicrobial Peptide CAD

The standard agar hole diffusion method with experimental samples of *Colibacillus* K88 and of *Flavous staphylococcus* is as follows:
   mix 20 μl of the bacteria suspension (OD600=0.2~0.3) with 25 ml LB solid culture medium at 55° C.
   coat on a plate,
   let solidify,
   with a sterilized hole puncher (diameter 5 mm) punch holes,
   add 20 μl of the expression supernatant to the holes for testing
   cultivate for 12 hours at 37° C.

The results are presented here below:
*Colibacillus* K88:
   inhibition zone diameter of 9.3 mm,
   bactericidal activity X=(9.3 mm-2.3 mm)/2=3.5,
   bactericidal titer (U/ml)=7000 U/ml;
   inhibition zone is shown in FIG. 1 (1), under the same expression conditions, 1A747 bacterial zymotic fluid is cultivated and its negative inhibition zone is compared.
*Flavous staphylococcus*:
   the inhibition zone diameter is 12.4 mm,
   bactericidal activity X=(12.4 mm-2.3 mm)/2=5.05,
   bactericidal titer (U/ml)=11000 U/ml;
   inhibition zone is shown in FIG. 1 (2).
*Salmonella bacilli*:
   the inhibition zone diameter is 5.8 mm,
   bactericidal activity X=(5.8 mm-2.3 mm)/2=1.75,
   bactericidal titer (U/ml)=3500 U/ml;
   inhibition zone is shown in FIG. 1 (3).
*Enterococcus faecalis*:
   the inhibition zone diameter is 3.9 mm,
   bactericidal activity X=(3.9 mm-2.3 mm)/2=0.8,
   bactericidal titer (U/ml)=1600 U/ml;
   inhibition zone is shown in FIG. 1 (4).
*Streptococcus faecalis*:
   the inhibition zone diameter is 6.1 mm,
   bactericidal activity X=(6.1 mm-2.3 mm)/2=1.9,
   bactericidal titer (U/ml)=3800 U/ml;
   inhibition zone is shown in FIG. 1 (5).

Example 3

Identification of the Antimicrobial Peptide CAD Excreted by Recombinant *Bacillus Subtilis* with Assembled Tris-Tricine SDS-PAGE The fermentation supernatant is filtrated with a United States MILLIPORE molecular weight cut off (MWCO) 10 KD ultra filtration tube, dialyzed with MWCO 2000 dialysis bags, and then freeze-dried to obtain *Bacillus subtilis* expression CAD products. A protein electrophoresis analysis is carried out using a 16% Tricine-SDS-PAGE and Coomassie Brilliant Blue G-250 concentration is also measured.

1. Preparation of 16% Polyacrylamide Gel (Separated Gel and Concentrated Gel)

|  | Separated gel | Concentrated gel |
|---|---|---|
| 30% polyacrylamide | 3.3 ml | 0.63 ml |
| Water | 2.09 ml | 1.6 ml |
| gel buffer | 2 ml | 0.75 ml |
| Urea | 2.16 g | — |
| 10% AP | 0.1 (unit) | 0.05 (unit) |
| TEMED | 10 μl | 5 μl |

2. Tricine-SDS-PAGE Protein Electrophoresis Reagent

| 10x anode buffer pH 8.9 | |
|---|---|
| Tris | 242.28 g |
| volume set 1000 ml with distilled water | |

-continued

| 10× cathode buffer pH 8.25 | |
|---|---|
| Tris | 121.1 g |
| Tricine | 179.16 g |
| SDS | 10 g |
| volume set 1000 ml with distilled water | |
| gel buffer pH 8.45 | |
| Tris | 121.0 g |
| SDS | 1 g |
| volume set 1000 ml with distilled water | |

3. Electrophoresis Experiment

Figure 2:
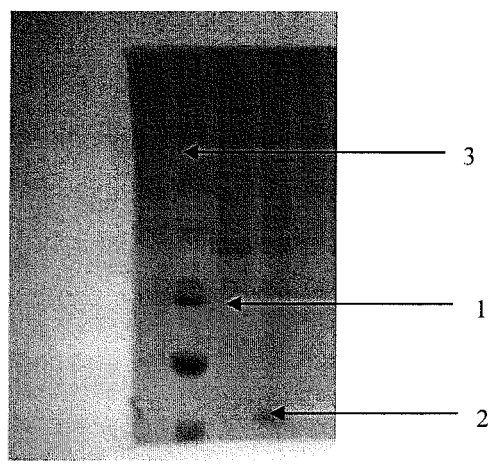
FIG. 2 shows the antimicrobial peptide CAD appraised by the 16% Tris-tricine SDS-PAGE;
1: control sample: freeze-drying 1A747 supernatant sample (0.25 mg/µl);
2: experimental sample: freeze-drying supernatant sample (0.25 mg/µl);
3: MARK (kDa): molecular weight (20.100, 14.400, 7.823, 5.856, 3.313)

The tricine-SDS-PAGE electrophoresis system is assembled through putting the cathode buffer solution into internal groove and the anode buffer solution into outside groove. The electrophoresis is carried out as follows: the voltage is set at 50V constant voltage for 5 hours. The gel is colored with Coomassie brilliant blue and incubated with glycerol. A picture of the gel is taken with gel imager photography. After the bromophenol blue indicator left the gel, the electrophoresis is stopped. Then the strip off of the gel and the discoloration are carried out according to conventional method. The results is shown on FIG. 2.

The results show that recombinant *Bacillus subtilis* can obviously secrete protein about 3.7 KDa, which is consistent with the theoretical size of CAD protein.

Thin-layer gel electrophoresis scanning images is analyzed by the software Band 5.0 and the result shows that the expression of proteins secreted by cell supernatant can be up to 39.9% of total protein.

Example 4

Content Confirmation of Antimicrobial Peptide CAD Secreted by Recombinant *Bacillus Subtilis* (BCA Protein Quantitative Measurement)

Fermentation of recombinant bacteria *Bacillus subtilis* 1A747: the fermentations supernatants are collected and pooled together according to their culture conditions filtrated with a United States MILLIPORE molecular weight cutoff (MWCO) 10 KD ultra filtration tube, and then dialyzed in MWCO 2000 dialysis bags. The protein content of each sample of supernatants is then calculated out, proportionally to the volume of each sample.

The invention claimed is:

1. A method of producing a recombinant antimicrobial peptide Cecropin AD (CAD) comprising the following steps:
   a. synthesizing the nucleic acid encoding a small ubiquitin-related modifier (SUMO) protease to produce a first synthetic DNA fragment;
   b. synthesizing the nucleic acid encoding the fusion protein of a *Saccharomyces cerevisiae* small ubiquitin-related protein with the antimicrobial peptide cecropin AD (CAD) to produce a second synthetic DNA fragment wherein said fusion protein comprises the amino acid sequence of SEQ ID NO:1;
   c. digesting the first synthetic DNA fragment from step a with the restriction enzymes EcoR I and BamHI, and digesting the second synthetic DNA fragment from step b with the restriction enzymes BamHI and SacI;
   d. subcloning the products from step c into vector pBluescriptII SK(+) in order to produce a D1778-1 plasmid;
   e. extracting the genome of *Bacillus subtilis* strain 168, and amplifying the highly active promoter p43 from the genome;
   f. sub-cloning the amplified promoter p43 into a T-vector for sequencing;
   g. introducing the promoter p43 from the T-vector into pGJ103 plasmid to produce pGJ284 plasmid;
   h. digesting the pGJ284 plasmid and the D1778-1 plasmid with restriction enzymes EcoRI and SacI, respectively;
   i. recovering the two restriction products from step h, and then ligating said two products with T4 DNA ligase in water-bath at 16° C. to obtain a recombinant pNF11 plasmid;
   j. transforming *Bacillus subtilis* 1A747 strain with said pNF11 plasmid to produce a recombinant *Bacillus subtilis* 1A747 strain which comprises said pNF11; and
   k. inducibly expressing said pNF11 which comprises the nucleic acid encoding the antimicrobial peptide CAD in the recombinant *Bacillus subtilis* 1A747 strain.

2. A *Bacillus subtilis* strain comprising the recombinant antimicrobial peptide cecropin AD (CAD) of claim 1, which is deposited at China General Microbiological Culture Collection Center with number CGMCC No. 2373.

* * * * *